United States Patent [19]

Grana

[11] Patent Number: 4,732,755

[45] Date of Patent: Mar. 22, 1988

[54] SKIN BURN TREATMENT

[75] Inventor: Luis Grana, Park Ridge, Ill.

[73] Assignee: University of Health Sciences/The Chicago Medical School, North Chicago, Ill.

[21] Appl. No.: 489,590

[22] Filed: Apr. 28, 1983

Related U.S. Application Data

[63] Continuation-in-part of Ser. No. 458,216, Jan. 17, 1983, abandoned, which is a continuation of Ser. No. 276,936, Jun. 24, 1981, abandoned.

[51] Int. Cl.$^4$ .............................................. A61K 31/78
[52] U.S. Cl. ........................................ 424/81; 514/953
[58] Field of Search ........................... 424/81, DIG. 13

[56] References Cited

U.S. PATENT DOCUMENTS

| | | | |
|---|---|---|---|
| 2,826,528 | 3/1958 | Shelanski et al. | 424/81 |
| 2,870,129 | 1/1959 | Merriam | 424/8 X |
| 3,577,516 | 5/1971 | Gould et al. | 424/46 |
| 3,579,628 | 5/1971 | Gander et al. | 424/28 |
| 4,272,518 | 6/1981 | Moro et al. | 424/81 |

OTHER PUBLICATIONS

Chemical Abstracts 81:38454m, 1974 (Iwao).
Chemical Abstracts 82:160257k, 1975 (Matsui et al.).
Chemical Abstracts 67:110245z, 1967 (Desmakais).

*Primary Examiner*—Leonard Schenkman
*Attorney, Agent, or Firm*—Norman Lettvin

[57] ABSTRACT

A new method for treatment of skin burn is disclosed. A known material, sodium polyacrylate, has been discovered to be useful in the treatment of burns. The method of treatment includes spreading sodium polyacrylate powder as a dressing over the skin burn area, and wetting the powder, such as by spraying with sterilized distilled water until the powder becomes moist. The outer wetted surface of the moistened powder layer dries to provide a parchment like surface. Such a dressing may be maintained in position over the skin burn area for about 2–3 weeks, operating to control loss of water from the body through the burn area, avoiding capillary permeability, and appearing to prevent infection of the burn area. The dressing may be selectively removed or is sloughed off, and is eventually pushed off by the growth of new tissue under the bottom surface of the protective layer. Sodium polyacrylate (PANa) may be used by itself, or mixed with an anti-inflammatory, or with an antibiotic. The appropriate antibiotic may be determined by culture and sensitivity testing of the site. PANa plus methylprednisolone was the most effective healing combination tested.

8 Claims, No Drawings

SKIN BURN TREATMENT

CROSS-REFERENCE TO RELATED APPLICATIONS

This application is a continuation-in-part of my co-pending application, Ser. No. 458,216, filed Jan. 17, 1983, now abandoned, the latter being a continuation of a prior-filed co-pending application, Ser. No. 276,936 filed June 24, 1981, and now abandoned.

FIELD OF THE INVENTION

This invention relates to a method of treating skin burn and to new use of a known substance having unexpectedly useful properties for the treatment of skin burns.

BACKGROUND OF THE INVENTION

Statement of the Problem

The skin is the largest organ of the mammalian body and normally serves several critical functions. One of the primary functions of intact human skin is the control of loss of water from the body and the prevention of bacterial infection. The intact skin of humans and mammalian animals serves as a highly efficient barrier to the evaporation of body water and the loss of body heat. The most external layer of the epidermis is cornified. It is a very effective moisture barrier and prevents evaporation of the body water.

Large burns destroy the water proof barrier, thus permitting dehydration of the body. A second immediate problem, caused within 12-24 hours after burns, is vascular injury. It has been shown that after thermal injury, capillary permeability is markedly increased. The capillaries become freely permeable with extravasation of fluid and proteins into the interstitial tissue.

Infection is another critical problem to deal with in the burned patient. Full-thickness skin burns largely diminish the protective mechanism of the skin against infection, and leaves necrotic tissue. The large amount of necrotic tissue represented by the burn scar serves as an ideal culture medium for bacteria growth.

Restitution, or avoidance of loss, of the foregoing three primary functions of the intact human skin, is the problem to be resolved in treating skin burns.

Brief Description of Prior Art

Burns are usually treated with dressings, whose most important qualities are: prevention of fluid loss; protection against heat loss; prevention of bacterial invasion and infection; providing for adequate contact maintained with wound to obtain an even, resilient compression against the wound; effecting a less painful removal of the dressing when necessary to change or remove the dressing; and maintenance of moisture beneath the dressing or covering which also aids in debridement. Dressings have included salves, vaseline, and bandages.

The common methods of treatment of second and third degree burns is through cloth dressings and grafts. Cloth dressings are usually used for minor burns. The advantages are that such dressings are easy to use and remove. Their disadvantages are that often a painful removal causes trauma to the patient.

Grafts are desirable because they show minimum infection, prevent water loss and protein loss, and are known to stimulate reepitheliazation. Grafts include: xenographs (pig skin), cadaver skin, autografts, amniotic membrane, and synthetic dressings.

As to xenographs, the advantages are they are inexpensive and easily obtainable. The disadvantages are: that a true "take" can not be obtained, and non-adherance causes necessary removal within 3-9 days after application.

As to cadaver skin, the advantages are: that it provides for a better take than with pig skin, and shows better healing. The disadvantages are that it can not be used as permanent covering, because it is only good for 15-25 days after appliction, and it is expensive and not easily available.

Autografts have the advantages: that they are useful for large open wounds, they function for extended periods of time, and obtain better "takes" than other types of grafts. The disadvantages are that donor sites are generally not available when wounds extend over 50% of the body surface.

An amniotic membrane has the advantages: that they are relatively inexpensive, and show good healing with takes similar to cadaver skin. The disadvantages are: that infections may develop, and they are not always available because they require special preparation.

Synthetic dressings have been suggested. One such dressing is a combination rubber and fiber collagen (Ref. I. V. Yannas, Science News, Jan. 3, 1981). Its advantages appear to be good contact to graft and wound surfaces; it prevents fluid loss and provides good protection against bacterial infection. It has the disadvantage of causing scarring.

Another synthetic dressing, known as "biobrane" has been reported upon by D. H. Frank, et al, Medical News JAMA, Dec. 5, 1980. Its advantages appear to be that it adheres well to wounds, and it prevents evaporation from exposed subcutaneous tissues. It has the disadvantage that control of bacteria has not been shown (Ref., Phillip Thompson, Chief Microbiology, Shriner's Burn Institute).

Another synthetic dressing is collagen sponge (Ref., Oluwainmi and Chvapil, Journal of Trauma, January, 1976). It appears to adhere well to the wound, and is good for early debridement thus effecting early wound healing, and no infection seemed to need covering.

Synthetic dressings are usually shown to be incapable of controlling growth between the surface of tissue and the synthetic dressing. (Ref., Phillip Thompson, supra).

OBJECTS OF THIS INVENTION

One object of this invention is to provide a treatment of skin burn that restores, to the area suffering from skin burn, the primary functions of intact human or animal skin, namely: as a water proof barrier; as protection against subdermal infection; and as a method for reducing capillary permeability after thermal injury.

Another object of this invention is to provide a substance having highly useful properties for the treatment of skin burns in humans and animals.

Still another object of this invention is to provide a substance that is readily available and is easily applied as a dressing of burns, and/or as a dressing of grafts, and which is relatively less expensive and/or more effective than other dressings.

Further objects and advantages will become apparent to one skilled in the art as this disclosure of my discovery proceeds.

BRIEF SUMMARY OF THE INVENTION

A known material, sodium polyacrylate, a powder which has long been used in the food industry as a thickening and sizing agent, has been found to be useful in treatment of skin burns. When mixed with water, it provides a jelly like substance which, when applied over a skin burn area, has been found to produce good healing. In an animal test only a single application was necessary for the entire healing process of the burn, which represents a definite advantage over conventional treatments which require several painful dressing changes.

DESCRIPTION OF PREFERRED EMBODIMENTS OF THE INVENTION

In the treatment of skin burns of animals and humans, it is proposed to provide a substitute skin consisting of a hygroscopic powder, namely sodium polyacrylate, with water added to form a uniform jelly-like layer which adheres firmly to, and covering the underlying area from which burned skin has been removed.

In the technique of treating the burn, after the area has been prepared for dressing, the powder is applied in sufficient amount to completely cover the area being treated with a continuous layer of powder. The powder is then wetted by spraying the powder layer with sterilized distilled water until the powder becomes moist. The moistness seeps through the powder layer to provide moistness adjacent the flesh that supports the powder layer, while at the same time the outer moistened surface of the wetted powder layer dries to provide a parchment like surface. The dressing remains in position for about two or three weeks and is eventually pushed off by the growth of new tissue under the bottom surface of the protective layer.

In a first modification, the hygroscopic material, such as sodium polyacrylate, in powder form is mixed or blended uniformly with an antibiotic powder, of the type normally used in treatment of infected third degree burns, to provide a mixture to be applied topically over the skin burn area. In preferred form the powder combination has water added thereto, by spraying as stated above, to form a uniform jelly-like layer which adheres firmly to, and covering, the underlying area of the skin burn. As is known in the art, a particular antibotic may be selected for mixing with the hygroscopic material by testing to determine which antibotic would be most effective against the infection existing at the wound being treated.

In a second modification, the hygroscopic material, such as sodium polyacrylate, in powder form, may be mixed or blended uniformly with an anti-inflammatory, or antipyretic, agent to provide a mixture to be applied topically over the skin burn area in the same way as described above for the combination which includes an antibiotic, the purpose being to provide anti-inflammatory or antipyretic-analgesic relief. Such anti-pyretic, anti-inflammatory agents may include aspirin, indomethacin, diclophenac sodium, or other known agents.

In a third modification, the hygroscopic powder, such as sodium polyacrylate, in powder form, either alone, or in a blended combination with an antibotic powder as described above, is applied topically over a skin graft that has been applied and with water added thereto, by spraying as disclosed above, to form a uniform jelly-like layer which adheres firmly to the underlying area of skin burn with skin graft thereon, to provide an improved method of fixation of the skin graft.

Sodium polyacrylate (abbreviation PANa) is a water soluble, high molecular compound. When moistened, or in acqueous solution, it is very viscous. It has long been known to an used in the food industry as a thickening agent, because of its high viscosity. When taken, or administered, orally it is hardly absorbed from the digestive tract, and is excreted into feces. It is practically nontoxic. Its structure is:

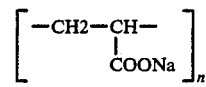

where n=degree of polymerization.

PANa occurs as a tasteless, odorless powder that is freely soluble in water. The characteristic of its aqueous solution is that the solution has a very high viscosity, compared with the aqueous solutions of other water-soluble, high-molecular compounds. The viscosity of the aqueous solution, however, will be reduced with a lower pH value and in the presence of salts. A characteristic of PANa is that it strings, which is not found with other water-soluble, high-molecular compounds. PANa agglutinates and precipitates protein in an acidic aqueous solution. The protein that has precipitated is hydrolyzed by pepsin and trypsin. The compound does not interact with carbohydrates or fats.

The physical chemical character of PANa is reportedly defined by the following features:

Mean molecular weight: $3,6 \times 10^6 \sim 5,5 \times 10^6$ (determined by light scattering method).

Solubility: It dissolves slowly in water to produce a very viscous solution. A 1% solution is slightly gelatinous at ordinary temperature. It is practically insoluble in organic solvents.

pH of acqueous solution: $8.0 \sim 9.0$ pKa: 4.82

Hygroscopicity: It is very hygroscopic.

Physicochemical properties of aqueous solution:

The physicochemical properties of PANa have been compared with those of the following 3 compounds which like PANa, are high-molecular, viscous compounds: Sodium alginate (AlgNa); Sodium carboxmethyl cellulose (CMCCNa); Polyethylene oxide (PEO).

(a) Viscosity: A 0.5% aqueous solution of PANa is about 60 times as viscous as sodium alginate, about 200 times as viscous as sodium carboxymethyl cellulose, and about 400 times as viscous as polyethylene oxide.

Viscosity of a 0.2% aqueous concentration of PANa has a viscosity of between $10^2$ and $10^3$ cp, and a 0.5% to 2.0% aqueous concentration of PANa has a viscosity that increases with increase of concentration of PANa in the solution, providing viscosity measurements in excess of $10^3$ cp and approaching $10^4$ cp with greater concentration of thickening agent in solution.

(b) Relationship between viscosity and pH value: The viscosity of PANa is low in acidity, but increases as the pH value rises from neutrality to alkalinity, while the viscosity of sodium alginate, sodium carboxymethyl celulose or polyethylene oxide remains practically invariable with a change in pH value. Because sodium alginate agglutinates to precipitate at a pH value below 5, and sodium carboxymethyl cellulose likewise agglutinates to precipitate at a pH value below 3, their viscosities cannot be precisely measured.

Experimentation has been conducted in Japan attempting to treat gastroesophageal ulcer in swine using PANa. This treatment has also led to a suggestion in Japan to use PANa as a therapeutic agent for human esophagities of various causes, e.g., postoperative reflux esophagitis, hiatal hernia esophagitis, and radiation esophagitis. Pharmacological studies have demonstrated that the compound is effective against the esophagitis (esopageal ulcer) that develops in rats due to reflux of bile and pancreatic juice after total gastrectomy, and that it was also effective against the esophageal ulceration due to gastric juice in rats.

Description Of Animal Test

Guinea pigs fasting for 25 hours have 3×2 inch area shaved. The animals were anesthetized with ether. Following this the exposed skin area was immersed in water at 80° C. for 10 seconds. This caused a third degree burn. Shortly after, the burned epidermis was removed by a gentle shearing force, exposing the subdermal area. After this, hygroscopic powder, sodium polyacrylate, was applied to half of the burned area. The other half was left alone for control. Water then was added to the powder to form a uniform jelly-like layer which adhered firmly, covering the underlying area. The animal was allowed to recuperate.

Immediate visible results were that the jelly-like layer of material adhered firmly onto the burn area. After 25 hours, the outer surface of the layer was dry and had a parchment-like consistency, thus forming an effective moisture barrier. In some cases water was added to the hardened surface, which then returned to a jelly-like consistency, demonstrating that the hygroscopic properties are still present.

Close-up pictures of the treated area clearly demonstrated a fine capillary network which indicates an active process of healing. This could not be seen in the untreated area.

This material adhered firmly to the skin for at least two weeks, at which time it begins to slough off.

It was found that only a single application of the material disclosed herein was necessary for the entire healing process of the burn. This represents a definite advantage over conventional treatments which require several painful dressing changes.

Foregoing portions of this C-I-P Specification were filed after tests had been performed on forty-five animals, with all yielding substantially similar results, and constituting the disclosure portion of my first application, Ser. No. 276,936, filed June 24, 1981.

Since said filing of Ser. No. 276,936 on June 24, 1981, a further reference and authority has come to my attention. This is the book "The Surgical and Medical Support of Burn Patients", by Bruce G. MacMillan, M.D., Chief of Staff, Shriners Burns Institute Cincinnati Unit, published by John Wright - PSG, Inc., Boston-Bristol-London 1982, (hereinafter "MacMillan"). MacMillan's section on Initial Basic Wound Care, at pages 79–87, including Table 12, at pages 84–85, entitled "Skin Substitutes for Temporary Wound Closures" describes the existing state of the art of treatment of burns. One new dressing is "Hydron", a product of Abbott Laboratories, whose use requires precautionary measures and which is described as an environmental barrier dressing. The components of the dressing are reported to be polyethylene glycol 400 U.S.P. and poly 2 hydroxyethyl methacrylate, and the dressing is described as translucent.

In 1982, using the same protocol as in my successful tests using PANa, I also tested polyacrylic acid, in powder form, in an attempt to treat skin burns, after it was suggested to me that the sodium salt of polyacrylic acid and polyacrylic acid itself are closely related chemically. The results of these tests were negative, as the test animals that were provided with a third degree immersion burn, and were then treated with polyacrylic acid, developed complications and died.

A further study, subsequent to the study that served as the basis of my first application, Ser. No. 276,936 will now be described.

Intact human skin serves as a highly efficient barrier to the evaporation of body water and loss of body heat. Third degree burns markedly impair this protective mechanism leaving the burned surface unprotected against infection, the burn eschar being an ideal culture medium for bacterial growth. This study investigated sodium polyacrylate (PANa), a nontoxic, high molecular, markedly hygroscopic, water soluble compound as a suitable dressing in third degree burns. Six groups of guinea pigs were treated with local applications of PANa powder immediately after removal of epidermis, and 48 hours after burn injury and eschar removal with the following preparations: PANa alone, PANa plus methylprednisolone, and PANa plus appropriate antibiotic. All preparations were in powder form.

Methylprednisolone is a cortico-steriod, that has anti-inflammatory properties, and is commercially available from Upjohn Co. in powder form, under the Trademark "SoluMedrol".

The antibiotic to be used was determined by culture and sensitivity tests from burns experimentally infected with *Streptococcus pneumoniae* and *Pseudomonas aeruginosa*. Skin biopsies were obtained to confirm that histological presence of and recovery from infection.

PANa preparations firmly adhered to the burned surface forming a jelly-like layer after spraying with distilled water mist. 24 to 48 hours later, this layer became thin and dry, however, the undersurface retained its jelly-like consistency. As the burn lesion healed, the PANa preparation layer sloughed off. PANa plus methylprednisolone mixture was most effective. PANa plus antibiotics healed infected burn areas. One single application of PANa for at least 10 days sufficed in most cases; second application was necessary only in spotted areas. It was concluded that PANa is an excellent dressing in third degree burns that protects against fluid and heat loss, diminishes dressing changes, and, most importantly, prevents and combats bacterial contamination.

When the applied layer of material is pushed off by the growth of new tissue, the growth appears to initiate from adjacent the outer edge of the layer and to work inwardly toward the center portion of the layer.

Subsequently, I had an opportunity of treating a human who had sustained a burn injury. On Jan. 2, 1983, in Peru, S.A., a Miss A.G., 27 years old sustained a second and third degree burn from steam on her right arm. The burn area was confined to the outer aspect of the right thumb, wrist, and lower aspect of the forearm. The second degree burn was confined mostly to the radial and medial aspec of the right forearm.

The patient was seen 24 hours after the accident. The bandage from the first-aid treatment was removed and the surface was cleaned with soap and water. The wound area was then throughly cleaned. A mixture of methylprednisolone powder (400 mgm.) mixed with sodium polyacrylate also in powder form, (1 GM.) was sprayed over the entire burn area.

After the application of this medication, the pain and burning sensation stopped and the patient did not complain any more during the entire treatment. The treated area was left without any cover. Twenty-four hours later it could be seen that the powder applied on the area of the second degree burn was falling off. Several blisters were forming in this area. The powder on the area of the third degree burn was firmly attached to the surface and was swelling, apparently from absorbing the exudate from the burn area.

Forty-eight hours later the wound looked almost the same. At this time the blisters were punctured with a sterile needle. After the fluid was drained, these punctures were sealed with PANa powder mixture. No attempt was made to remove the skin covering this area. Five to six days later it became loose and was removed without any discomfort to the patient. The powder mixture on the third degree burn was still firmly attached but the smooth, continuous surface was developing cracks separating the whole area into small fragments. As soon as these cracks developed additional small amounts of the powder was applied to avoid any exposure of the burn surface.

By the beginning of the second week the separation of this layer of medication from the burn surface could be seen. This was noticed in the same way as the experiments—starting at the edge of the burn surface.

By the twentieth day, the entire burn area was left uncovered, leaving a nice, smooth, discolored area of skin free of scar. As time went on the burn surface was slowly recovering to its normal color and appearance.

It should be emphasized that no antibiotics were added, locally or internally. Also the entire treatment was done in open with no bandages or coverings of any kind. Once in a while the patient complained of tightness on the area covered by the powder. It was observed that the powder was drying. So, the entire area was immersed in water and the gelatinous consistency returned as was seen in the experiments. Once this was accomplished the patient was relieved of the tightness sensation.

In summary: A small third degree burn of a human was treated locally with a mixture of PANa and methylprednisolone. The healing started by the second week and terminated by the third week. No bandages were applied and no dressing changes were needed during the entire healing period.

While there has been disclosed several particular embodiments of my invention, the inventions intended to be covered by this invention will be understood, by one skilled in the art, as limited solely by the claims appended hereto.

What is claimed and desired to be secured by Letters Patent of the United States is:

1. A method of treatment of human or mammalian animal skin burn by providing a substitute skin protective dressing over the area of skin burn, comprising the steps of: applying onto the entire area of skin burn a layer of powder that is water soluble and hygroscopic and whose principal ingredient is sodium polyacrylate having a mean molecular weight of $3.6 \times 10^6 \sim 5.5 \times 10^6$, in powder form; then wetting the layer of powder with water to provide a highly viscous jelly-like layer that adheres firmly to the skin burn area; and the outer surface of the layer drying thereafter to form an outer surface of parchment-like consistency.

2. A method as in claim 1 wherein the highly viscous layer includes sodium polyacrylate provided in powder form and exposed so that the outer surface of the viscous layer will dry.

3. A method as in claim 1 wherein the substitute skin is maintained in position on the skin burn area for a period of between 10 and 20 days, maintaining moistness adjacent the flesh.

4. A method as in claim 1 wherein the wetting of the layer of powder is effected by spraying water onto the layer of powder until the powder becomes moist, the moisture seeping through the powder layer to provide moisture adjacent the flesh that supports the powder layer, while the exposed outer surface of the powder layer dries to provide a parchment-like surface.

5. A method as in claim 1 including simultaneous application to the skin burn area of a topical application of an antibacterial agent that is mixed into the viscous jelly-like layer.

6. A method of treatment of a skin burn area to which has been applied a skin graft, including the step of applying a layer that includes wetted sodium polyacrylate, the sodium polyacrylate, before wetting, being in powder form and having a mean molecular weight of $3.6 \times 10^6 \sim 5.5 \times 10^6$, over the skin graft to aid in fixation of the skin graft to the skin burn area.

7. A method of treatment of human or mammalian animal skin burn, comprising the steps of:
  supplying a substitute skin protective dressing which restores to an area suffering from skin burn the primary functions of intact skin, namely a water proof barrier, to prevent fluid loss from the body and to serve as protection against subdermal infection and for reducing capillary permeability after thermal injury, by applying to the area requiring a substitute skin, a continuous layer of water-soluble, high-molecular weight, hygroscopic powder whose principal ingredient is sodium polyacrylate powder having a mean molecular weight of $3.6 \times 10^6 \sim 5.5 \times 10^6$;
  wetting said powder with water to provide a highly viscous, jelly-like, continuous layer that adheres firmly to and covering the skin burn area, and provides moisture adjacent the flesh in the skin burn area; and
  permitting the outer surface of the wetted layer to dry to form an outer surface of parchment-like consistency which prevents loss of liquid outwardly therethrough.

8. A method of treatment as set out in claim 7 including the step of maintaining the dressing in position until it is eventually pushed off by the growth of new tissue under bottom surface of the layer.

* * * * *